United States Patent
Guseva et al.

(10) Patent No.: US 6,454,797 B2
(45) Date of Patent: Sep. 24, 2002

(54) TETRACARBON

(75) Inventors: Malvina B. Guseva, Moscow (RU);
Nikolay D. Novikov, Moscow (RU);
Vladimir G. Babaev, Moscow (RU);
Arnold A. Adamyan, Moscow (RU);
Igor A. Lavygin, Moscow (RU)

(73) Assignee: Tetra Consult Limited, Moscow (RU)

( * ) Notice: Subject to any disclaimer, the term of this patent is extended or adjusted under 35 U.S.C. 154(b) by 0 days.

(21) Appl. No.: 09/929,968

(22) Filed: Aug. 14, 2001

Related U.S. Application Data

(62) Division of application No. 09/101,614, filed as application No. PCT/IB96/01487 on Dec. 18, 1996, now Pat. No. 6,355,350.

(30) Foreign Application Priority Data

Jan. 12, 1996 (RU) .......................................... 96100628

(51) Int. Cl.[7] .................................................. A61F 2/24
(52) U.S. Cl. ......................... 623/2.1; 428/408; 623/1.1; 623/3.1; 623/11.1; 604/265
(58) Field of Search .................. 604/265; 623/11, 623/66, 901, 1, 2, 16, 18, 20; 428/408

(56) References Cited

U.S. PATENT DOCUMENTS

| | | | |
|---|---|---|---|
| 4,248,909 A | 2/1981 | Whittaker | 427/249 |
| 5,073,241 A | 12/1991 | Watanabe | 204/192 |
| 5,122,249 A | 6/1992 | Niemann et al. | 204/192 |
| 5,133,845 A | 7/1992 | Vallana et al. | |
| 5,364,690 A | 11/1994 | Takahashi et al. | 428/408 |
| 5,427,827 A | 6/1995 | Shing et al. | 427/575 |
| 5,455,081 A | 10/1995 | Okada et al. | 427/528 |
| 5,516,884 A | 5/1996 | Bianconi | 528/397 |
| 5,716,708 A | 2/1998 | Lagow | 428/408 |
| 5,725,573 A * | 3/1998 | Dearnaley | 623/2 |
| 5,776,602 A | 7/1998 | Ueda et al. | 428/408 |
| 5,984,905 A * | 11/1999 | Dearnaley | 604/265 |
| 6,171,343 B1 * | 1/2001 | Dearnaley | 623/1 |
| 6,221,108 B1 * | 4/2001 | Smith | 623/16.11 |

FOREIGN PATENT DOCUMENTS

| | | |
|---|---|---|
| EP | 0 102 328 A | 3/1984 |
| GB | 2 286 347 | 8/1995 |

OTHER PUBLICATIONS

Rother, B. et al., 1990"Cathodic Arc Evaporation of Graphite with Controlled Cathode Spot Position", *Thin Solid Films*, 188(2):293–300.

Gupta B.K. et al., 1995 "Micromechanical Properties of Amorphous Carbon Coatings Deposited by Different Deposition Techniques", *Thin Solid Films*, 270(1/02) 391–398.

* cited by examiner

*Primary Examiner*—Archene Turner
(74) *Attorney, Agent, or Firm*—Morrison & Foerster LLP

(57) ABSTRACT

A synthetic polymeric form of carbon (Tetracarbon™) which exhibits some properties similar to biological tissues. Tetracarbon is highly biocompatible and may have application in medicines and microelectronics. Tetracarbon is a biocompatible substrate coating made by depositing short linear chains of carbon stores upon the surface of the substrate. The carbon chains are non-turbostratic and oriented perpendicular to the substrate surface and are densely packed parallel to one another in hexagonal structures with the distance between the carbon chains being between 4.8–5.03 ANG.. A layer of Tetracarbon is identical to an adjacent layer and randomly shifted laterally relative to each other.

7 Claims, 4 Drawing Sheets

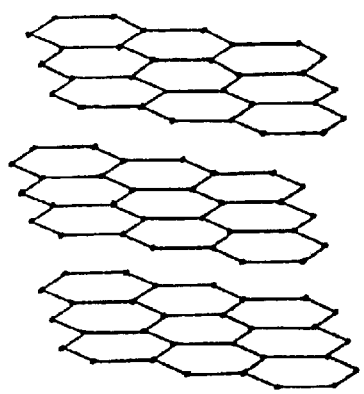
Fig 1(a)
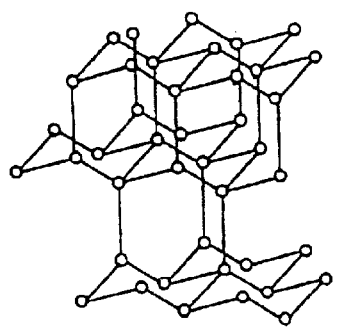
Fig 1(b)
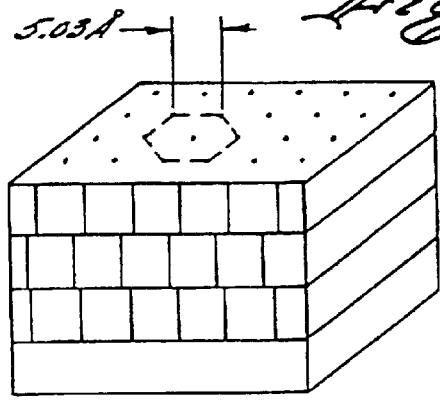
Fig 1(d)
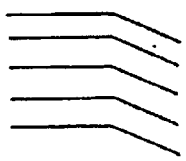
Fig 1(e)
Fig 1(c)
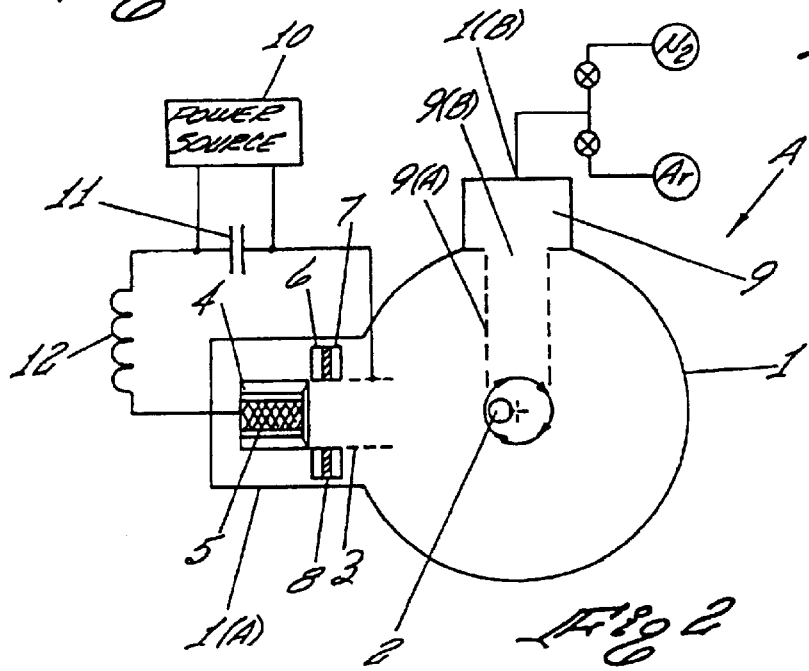
Fig 2

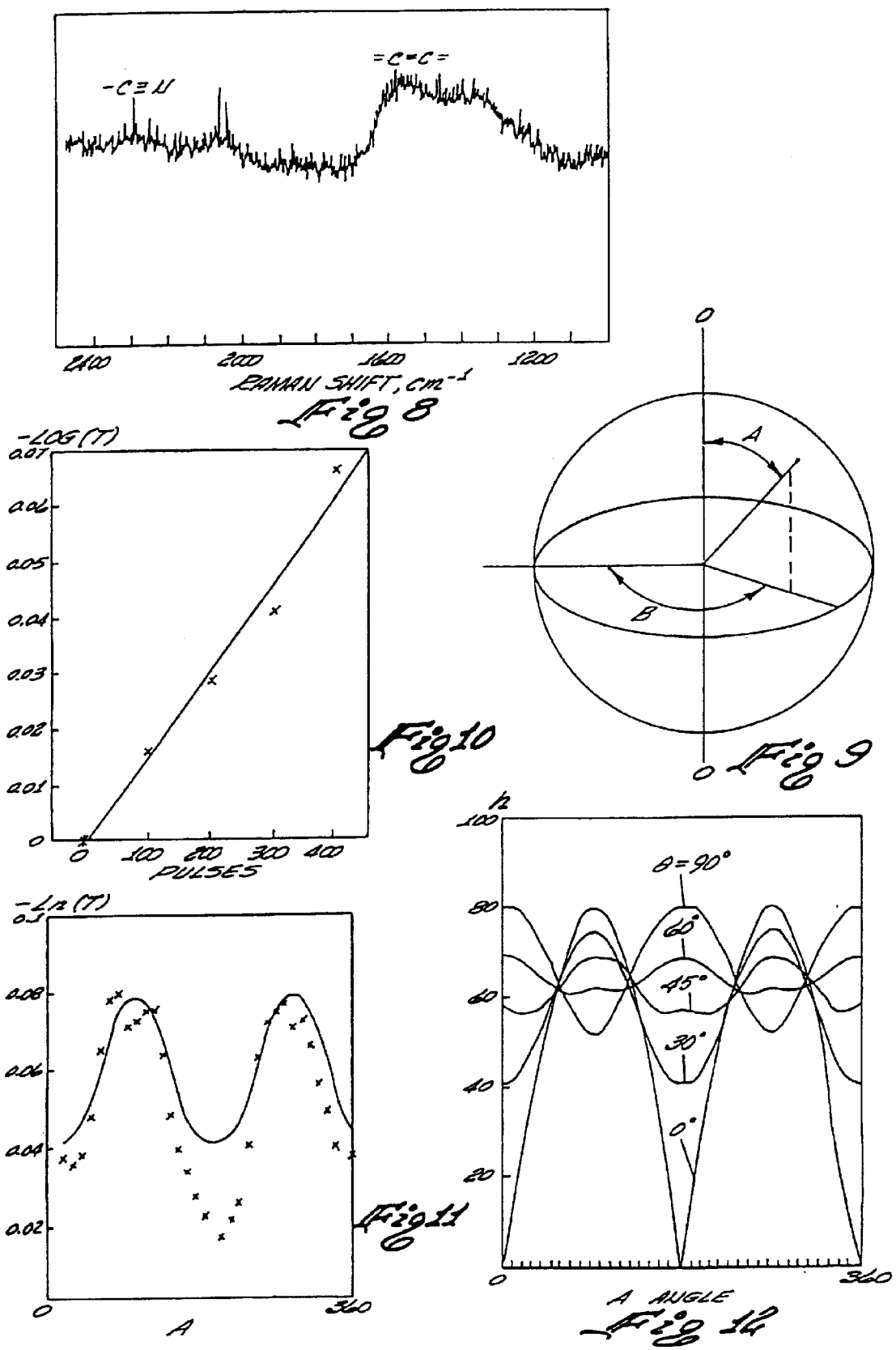

TETRACARBON

CROSS-REFERENCE TO RELATED APPLICATION

This application is a divisional of U.S. Ser. No. 09/101,614 filed Mar. 23, 1999, now U.S. Pat. No. 6,355,350 which is a 371 of application Ser. No. PCT/IB96/01487, filed Dec. 18, 1996.

BACKGROUND OF THE INVENTION

1. Field of the Invention

The invention relates to biocompatible carbonaceous films for applications including medical implantation and to a method for fabricating the films on a substrate surface.

2. Prior Art

Elemental carbon occurs naturally in two widely known allotropic forms: diamond and graphite, each of which exist in more than one polymorphic modification. Diamond is a 3-dimensional spatial polymer of tetrahedral carbon in which every carbon atom is bonded to four other carbon atoms by four identical bonds, each 1.54 Å, long. Diamond, which is a dielectric, has a minimal structural unit consisting of a tetrahedron, with carbon atoms occupying positions in each of the tetrahedron's corners and at the center of the tetrahedron.

Graphite consists of one or more 2-dimensional (planar) polymer sheets of trigonal carbon wherein the polymeric sheets form parallel layers. Each carbon atom is bonded to three other carbon atoms with three identical bonds evenly distributed in a plane, each bond being 1.42 Å long. The identical overlying graphite layers are oriented parallel to each other and are located at a distance of 3.35 Å from each other. Graphite is a conductor of electric current. The 6-carbon benzene ring is the basic structural unit of graphite.

Carbyne is the third known allotropic form of polymeric carbon. The structure of carbyne is the most similar to the structure of Tetracarbon™, the polymeric form of carbon referred to hereinafter as Tetracarbon, which comprises the subject matter of the present invention and is defined. Carbyne is a semiconductor formed from linear polymeric carbon. A straight carbon chain is the basic structural element within a carbyne layer in which every carbon atom is bonded to two neighbors with two equal bonds, wherein each bond is between 1.19–1.38 Å long and the distance between carbon chains is 2.97 Å. A minimal structural unit from which a carbyne crystal can be assembled is a hexagonal prism. Bent chains are located in the corners of the hexagon. Bendings divide the prism into two parts. A straight chain is located in the center of the lower part with a comparable chain being absent in the upper part. Admixture of hetero (non-carbon) atoms may result in such hetero atoms occupying this vacancy. Carbyne was obtained for the first time in 1969 by means of oxidizing polydehydrocondensation of acetylene. Carbyne forms a sheet-like microcystal consisting of a plurality of regularly shifted chemically bonded A-B-A-B . . . layers. Each A layer comprising the microcrystal consists of densely packed carbon chains oriented perpendicular to the plane of the layer and sandwiched between two B layers. A and B layers are regularly shifted relative to each other and chemically bonded to adjacent layers. In each B layer there is a regular grating of chain vacancies. At present, no carbyne crystals are known having a size greater than 1 μm (Bulletin of the Russian Academy of Science. Physics, 1993, vol. 3, p. 450).

In addition to the pure crystalline allotropic forms of carbon described above, there are a number of intermediate transitional forms such as pyrolytic carbon and glassy carbon. Pyrolytic carbon is a synthetic high-density carbon polymeric with turbostratic structure and composed of either pure or silicon-alloyed carbon microcrystals. These properties distinguish pyrolytic carbon from other polymeric carbon materials such as graphite, diamond and glassy carbon. Short range order in a pyrolytic carbon film which presents a turbostratic structure wherein the carbon chains are in a plane parallel to the plane of the film and is similar to that of graphite; the basic structural unit being 6-carbon slightly-deformed benzene rings. Pyrolysis of a gaseous hydrocarbon is employed for depositing pyrolytic carbon upon a substrate surface. The high temperature required for pyrolytic deposition limits the choice of substrate to materials to those which are stable at high temperatures such as ceramics and low-porosity graphite. In addition, a substrate composed of a brittle material such as graphite must first be mechanically shaped prior to coating. Due to the extreme hardness of pyrolytic carbon, it can only be worked and polished with diamond tools and pastes so that only relatively simple shapes are suitable for graphite substrates.

Vapor deposition has been used to transfer carbon atoms from a turbostratic carbon target to a substrate such as the surface of an implantable prosthesis. By appropriately regulating the conditions under which carbon deposition takes place, it is possible to hold the temperature of the substrate below a predetermined limit so as to minimize or prevent altering the substrate's physical characteristics. Vapor deposition allows carbon to be deposited in a thin film upon a substrate surface, the film forming a coating which retains the turbostratic structure and high-density characteristic of pyrolytic carbon.

Representative patents and author's certificates describing various prior art carbon coatings, including turbostratic coatings, are presented below in Table 1.

TABLE 1

| Country | Number | Title |
| --- | --- | --- |
| U.S.S.R. | a.c. 1837620 | The method of plasma-spraying of bio-active coatings |
| | a.c. 165628 | The method of manufacturing of free nickel films |
| | a.c. 646578 | The method of manufacturing of thin films |
| | a/c. 1163656 | The method of plasma reactive spraying of films in vacuum |
| | a.c. 1405361 | The appliance for ion-plasma processing of substrates in vacuum |
| | a.c. 1750270 | The method of manufacturing of films and the appliance for its realization |
| | a.c. 1710596 | The method of carbon-based films manufacturing |
| | a.c. 1710596 | Pulse generator of carbon plasma |
| | a.c. 1809840 | The appliance for thin films deposition in vacuum |
| | a.c. 336981 | The appliance for deposition of films by means of cathode spraying |
| | a.c. 603701 | The appliance for manufacturing of metal, semiconductor, and dielectric films, in particular, of the artificial diamond coatings by the method of cathode spraying |
| U.S.A. | U.S. Pat. No. 5270077 | The method of chemical deposition of plane diamond film from vapor phase |
| | U.S. Pat. No. 5133845 | The method of prostheses manufacturing from polymer materials with bio-compatible carbon coating |
| | U.S. Pat. No. 5073241 | The method of formation of carbon films and the appliance for its realization |
| | U.S. Pat. No. 5073241 | The method of formation of carbon films |
| | U.S. Pat. No. 5078837 | The method of ion deposition of coating and the appliance for its realization |
| | U.S. Pat. No. 4981568 | The method of manufacturing of diamond films of high purity at low temperatures and the appliance for its realization |

TABLE 1-continued

| Country | Number | Title |
|---|---|---|
| France | patent 2675517 | The method of deposition of diamond-like layer and an object covered with such layer |
| Japan | patent 5-26867 | The method of manufacturing of hard carbon film |
| | patent 5-10426 | Hard carbon film |
| | patent 5-10425 | The method of manufacturing of thin carbon film |
| | patent 5-40825 | The method of formation of hard carbon film |
| | patent 5-42506 | The device for vacuum spraying of films |
| | patent 5-43783 | The device for deposition of film coating |
| | patent 3-177567 | The appliance for vacuum spraying of films |
| | patent 3-15846 | The method of formation of carbon coating with diamond-like structure |
| | patent 3-6223 | The method and appliance for formation of carbon coating transparent for infrared beams |
| PCT | 2/09715 | The method of plasma spraying of biologically active coatings on implants |
| European | 0467043 | Diamond film without a substrate, the method and appliance for its manufacturing |
| | 0474369 | Coating made of diamond-like carbon |
| | 0500359 | Carbon with graphite structure its interpolation derivatives and the methods of their production |
| | 0474369 | Coating made of diamond-like carbon |
| | 0420781 | The method of manufacturing of a carbon-based material |

A method for manufacturing a polymeric prosthesis having a biocompatible carbon coating is shown in U.S. Pat. No. 5,133,845. The biocompatible carbon coating is deposited on the substrate surface by means of triode cathode spraying. Carbon is sprayed at low temperature at a pressure ranging from $6 \times 10^{-4}$-$6 \cdot 10^{-3}$ mbar ($6 \times 10^{-2}$-$6 \times 10^{-1}$ Pa). Spraying voltage is 2000-3200 V, the spraying current being between 0.1–0.3 Amperes. A uniform biocompatible coating of turbostratic carbon is formed upon the substrate surface with the density of the coating being at least 2.1 g/cm$^3$.

Another method for manufacturing a prosthesis having a biocompatible film coating is presented in U.S. Pat. No. 5,084,151. The coating deposition proceeds in a vacuum chamber at a pressure of $10^{-4}$–$10^{-2}$ mbar. A plasma beam is formed and directed toward a carbon cathode disposed to lie in the path of the plasma beam. High voltage at low current is applied to the cathode. The sprayed carbon atoms are directed toward and impinge upon the substrate surface which is heated to a temperature of 250° C. The coating obtained by this method also has turbostratic structure.

A turbostratic carbon polymer film can be applied to the outer surface of a prosthesis in an apparatus comprising a power supply and a vacuum chamber partitioned to form two sub-chambers. A gaseous ion source directs an ion beam through an aperture in the first sub-chamber into the second sub-chamber. In the second sub-chamber, which is open to (in gaseous communication with) the first sub-chamber, a carbon cathode is located directly in the path of the ion beam. A ring-shaped anode surrounds the carbon cathode. A heat transfer system is employed for cooling the carbon cathode and anode. The carbon cathode is sprayed with the ion beam and carbon is vaporized. The substrates to receive the coating are placed within the second sub-chamber and disposed to receive the carbon vapor on the surface thereof upon carbon vapor condensation. This method and apparatus produces a turbostratic carbon film which is deposited upon a substrate surface to form a coating on the substrate which is reported to exhibit biocompatible properties.

Carbyne coating has been reported to posses high biocompatibility and thromboresistivity (Diamond and Related Materials, v.4 (1995) p. 1142–44). Carbyne coatings, fibers and films are prepared by the chemical dehydrohalogenation of halogen-containing polymers such as, for example, polyvinylidene fluoride ("PVDF"). An alkaline alcoholic solution is used as the dehydrohalogenating agent. However, such carbyne coatings can be produced only on the surface of PVDF substrates which limits its applications.

A method for effecting the ion-stimulated deposition of carbyne on a substrate surface is known (Bulletin of the Section of Physics of the Academy of Natural Sciences of Russia, no. 1, 1993, p. 12). The method relies on the ion-stimulated condensation of carbon in high vacuum ($10^{-7}$ Torr). A flowstream of carbon and a flowstream of ions of inert gas (e.g. argon), either simultaneously or sequentially, are directed to impinge upon the substrate surface. The carbon flux is obtained by means of thermal evaporation or ion spraying of graphite. The energy of the argon ions (Ar$^+$) bombarding the substrate surface may vary, but for deposition is generally within the energy interval between 90 up to 200 eV. The current density of ions at the substrate is 10–1000 $\mu$A/cm$^2$, the rate of film growth is 10–1000 Å/min, and the thickness of the deposited film is 200–1000 Å. Carbyne films are obtained by means of irradiation with ions either simultaneously or alternating with condensation of carbon. The resulting films are quasimorphous, consisting of an amorphous carbon matrix and microcrystalline impurities. The method is inoperable for coating surfaces having either a relatively large area and/or a complex shape, and may be applied only for the deposition of films on conducting or semiconducting substrate surfaces. The method is inoperable for depositing carbyne on the surface of substrates such as ceramics, non-conducting polymers and silicone rubber which are substrate materials commonly used for manufacturing medical implants.

In summary, the prior art does not provide either an apparatus or a method for depositing a non-turbostratic carbon film having a structure as described below or an apparatus operable for depositing a non-turbostratic carbon film on a large surface, wherein the film exhibits the properties characterizing Tetracarbon which are more fully disclosed below.

SUMMARY OF THE INVENTION

It is an object of the invention to provide a biocompatible coating for a surgically implantable article.

It is a further object of this invention to provide a non-turbostratic carbon film adapted for coating a substrate surface.

It is a further object of the invention to provide a method for making a prosthesis or similar surgically implantable device which has a biocompatible tissue-contacting coating on the outer surface.

It is yet a further feature of the invention to provide an apparatus which is operable for depositing a non-turbostratic biocompatible polymeric coating upon the surface of a substrate.

A further objective of the invention is to provide a coating for a surgically implantable medical device wherein the coating is adapted to permit self-reassembly in order to accommodate tissue ingrowth.

Tetracarbon is a polymeric carbon film having a non-turbostratic 2-dimensional planar structure. In Tetracarbon films the short, straight linear carbon chains that form the layer are organized into densely packed hexagonal structures with the distance between chains being 4.8–5.03 Å. Unlike turbostratic carbon films, in Tetracarbon film the long axis of the linear carbon chains comprising the film ares oriented perpendicular to the plane of the film. A Tetracarbon film may be a single layer or many layers which overlie one another. If the number of layers in a Tetracarbon film exceeds one, the layers are identical and randomly shifted relative to each other. In Tetracarbon, the interaction between the linear carbon chains in the film is due to van der Waals forces which set the distance between the chains in the range 4.8–5.03 Å. As is true with carbyne, a carbon chain is the main structural element of Tetracarbon. The Tetracarbon chain consists substantially entirely of carbon atoms, each carbon atom having two 1.19–1.38 Å-long valence bonds with a 180° angle between them. The introduction of hetero atoms into a carbon chain under the influence of ion irradiation and alloying can modify the structure of Tetracarbon be to adapted to particular applications. The morphological features characterizing a Tetracarbon coating can be modified, for example by:

(a) regular joining of chains within adjacent layers;
(b) splitting of a chain into linear fragments; and/or
(c) formation of bends within a carbon chain; and/or
(d) changing the distance between carbon chains.

The length of linear carbon chain fragments and the number of bends effect the morphology of Tetracarbon. Thus, the morphology may be varied by the choice of gas used for ion irradiation, the composition using an admixture of gases and varying the proportions of the admixture and the temperature of deposition. Tetracarbon structure may "self-organized" in vivo; structurally readjusting to adapt itself to the structure of a protein molecule growing on and intimately into the Tetracarbon due to the interaction between the film and the protein penetration of endogenous ions into the Tetracarbon layer.

The above objectives are met with a polymeric carbon film referred to herein as Tetracarbon. Tetracarbon refers to a carbonaceous polymeric film, the surface of the film defining a plane. The film may be either a single layer or a superimposition of multiple layers wherein each layer within the film consists essentially of a plurality of linear chains of covalently bonded carbon atoms. The linear (end to end) axis of each linear carbon chain in a layer is perpendicular to the plane of the film surface. Thus, Tetracarbon is a non-turbostratic material. Only one end of the carbon chains comprising the innermost layer of Tetracarbon may be bonded to the surface of the substrate upon which the Tetracarbon layer is deposited. The opposing end of the carbon chains project away from the substrate surface in a substantially vertical direction.

An apparatus operable for depositing a Tetracarbon coating upon a substrate surface comprises essentially a vacuum chamber inside which are disposed in combination: a graphite cathode of main discharge, an anode of main discharge; an ignition electrode, a cathode of auxiliary discharge separated from the ignition electrode by a dielectric spacer; and a power supply. The vacuum chamber has two side compartments, each of which are in gaseous communication with the interior of the vacuum chamber by means of apertures therebetween. One of the two side compartments contains the cylindrical graphite cathode of main discharge and the anode of auxiliary discharge, surrounding the cathode of main discharge with a gap therebetween. The end of the cylindrical anode of auxiliary discharge closest to the substrate has a conic shear directed axially inward and facing the cathode of main discharge. The anode of the main discharge comprises two or more electrically conductive parallel rings which are rigidly connected to one another by metal rods. The ignition electrode, dielectric spacer, and the cathode of the auxiliary discharge are fabricated as a laminated ring, each of the elements being rigidly affixed to each other and interposed between the anodes of the main and auxiliary discharges. The anode of auxiliary discharge, cathode of main discharge, ignition electrode, cathode of auxiliary discharge, dielectric spacer and anode of main discharge are coaxially disposed with respect to each other.

A substrate holder, placed inside the vacuum chamber behind the anode is adapted to support a substrate and permit planetary rotation of the substrate around two axes and is connected electrically to the chassis ground of the vacuum chamber. The axis around which the substrate holder revolves is tilted or inclined with respect to the orbital axis. An aperture in the wall of the second side compartment of the vacuum chamber permits entry of an ion beam into the vacuum chamber. The ion and plasma beams intersect at the substrate surface. The apparatus also includes a capacitor and an inductance, one pole of the inductance being connected to the cathode of main discharge and the other pole being connected to a negatively charged plate of the capacitor, the positively charged plate of which is connected to the anode of main discharge. The poles of the power supply are attached to the corresponding plates of the capacitor. The cathode of main discharge is made of graphite having high purity. For medical applications, a purity of 99.99% or better is preferred.

While the above summary of the invention generally sets forth the nature of the invention, the features of the invention believed to be novel are set forth with particularity in the appended claims. However, particular embodiments of the invention, both as to organization and method of operation, together with further objects and advantages thereof may best be understood by reference to the following description taken in conjunction with the accompanying drawings in which:

BRIEF DESCRIPTION OF THE DRAWINGS

FIG. 1A is a schematic drawing showing the atomic distribution in graphite.

FIG. 1B is a schematic drawing showing the atomic distribution in diamond.

FIG. 1C is a schematic drawing showing the atomic distribution in carbyne. 1 identifies the chain vacancies; 2 indicates regular bends between the layers; A refers to a densely packed layer; and B indicates a layer with chain vacancies.

FIG. 1D is a schematic drawing showing the atomic distribution of carbon atoms in a non-turbostratic polymeric carbon film (Tetracarbon).

FIG. 1E is a hypothetical model of a Tetracarbon chain with two bends, which illustrates the possible random shift of Tetracarbon layers.

FIG. 2 is a schematic drawing of an apparatus operable for depositing a Tetracarbon coating upon the surface of a substrate.

FIG. 8 is the Raman spectrum of Z-type layer of film impregnated with nitrogen atoms.

FIG. 9 shows a spherical coordinate for a point on the surface of a spherical substrate being coated.

FIG. 10 is a graphical presentation illustrating the dependence of the thickness of the coating (−log T) on the number of pulses applied to the graphite cathode of main discharge.

FIG. 11 shows the dependence of the thickness of a layer of Tetracarbon on the angle A (FIG. 9).

FIG. 12 shows the theoretically calculated curves for the coating thickness as a function of A for different values of θ (FIG. A).

DESCRIPTION OF THE PREFERRED EMBODIMENTS

Figure 3:
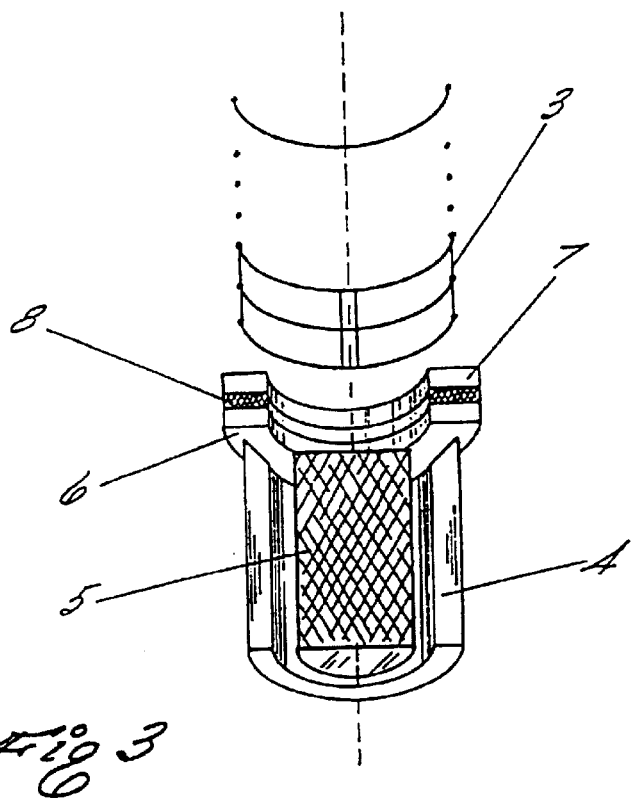
FIG. 3 is a top cutaway perspective view of the electrode assembly (3-4-5-6-7-8) of FIG. 2.

The term Tetracarbon, as used herein, refers to a polymeric film formed as a coating on a substrate wherein the film has at least one layer comprised essentially of a plurality of carbon chains and wherein only one end of a chain is bonded to a substrate surface, the plurality of carbon chains being parallel to each other and being oriented generally perpendicularly to the surface of the layer. The linear carbon chains of Tetracarbon are parallel and densely packed into hexagonal structures with the distance between the chains being between 4.8–5.03 Å. If there is more than one layer, the layers are identical and statistically shifted relative to each other.

For coating the surface of medical devices for implantation, Tetracarbon is preferably obtained by evaporation of graphite from a graphite target having a purity of better than 99.99%. In the present apparatus, the evaporation of graphite from a graphite electrode is performed by pulse arc discharge in a vacuum chamber. Depending upon the particular electron energy, the geometry of the apparatus, voltage, current and ions present in the gaseous discharge, compensated currentless plasma sheaves are formed around the cathode. The compensated currentless plasma sheaves formed around the cathode have a density of around $5 \times 10^{12}$–$1 \times 10^{14}$ cm$^{-3}$, for a pulse duration of 200–600 µs, and a pulse repetition rate of 1–5 Hz. A beam of ions of and inert gas, preferably argon (or an admixture of gases comprising an inert gas such as argon), having an energy of 150–2000 eV is directed to intersect the flow of compensated currentless sheaves of carbon plasma at the surface of the substrate. The substrate surface is positioned within a vacuum chamber at the intersection of the ion beam and carbon plasma flow stream. Tetracarbon deposits upon the substrate surface as layer-forming linear carbon chains oriented substantially perpendicular to the plane of the adjacent surface of the substrate at a temperature between 0°–200° C., depending on the substrate. For a silicone substrate, a surface temperature in the range of 20°–50° C. is preferred. When the number of layers of Tetracarbon in a Tetracarbon coating is more than one, each layer is parallel to one another, identical and randomly shifted relative to the adjacent underlying layer. While argon is preferably used as the inert gas with the argon-partial pressure inside the vacuum chamber being in the range $1 \times 10^{-1}$–$1 \times 10^{-2}$ Pa, other pressures and/or gases may be preferred for the ion beam for other substrates and/or applications.

With reference to FIG. 2, a schematic view of an apparatus operable for making Tetracarbon is shown. The apparatus A includes a vacuum chamber 1, the chassis of which has two side compartments or chambers 1A and 1B in which carbon chain plasma beams and ion beams are respectively formed, their respective beam axes intersecting within the interior 1A of the vacuum chamber. Inside chamber 1A, a cylindrical cathode of main discharge 5 and an anode of auxiliary discharge 4 are located, the latter being tubular and surrounding the cathode of main discharge 5 with a gap therebetween. One end of the anode of auxiliary discharge 4 is beveled inwardly at about 45° to provide a surface which faces both the cathode of main discharge 5 and the ignition electrode 6. The anode of main discharge 3 is formed from two parallel rings rigidly connected to one another by metal rods (not shown in FIG. 2) equally spaced around the perimeter of the rings. The ignition electrode 6, dielectric spacer 8, and the cathode of the auxiliary discharge 7 are made as a laminate annulus or ring, the elements 6, 8 and 7 rigidly connected to each other and laminated ring 6, 8, 7, placed between the anode of main discharge 3 and auxiliary discharge 4.

The substrate holder 2 is positioned within the vacuum chamber 1, the holder 2 being adapted to provide planetary rotation of a substrate around a vertical axis. The substrate holder is electrically connected to the chassis of vacuum chamber 1. The substrate is preferably electrically isolated from the substrate holder; maintained at a floating voltage and at a temperature between 20°–50° C. Condensation of carbon chains from the currentless carbon plasma upon the substrate surface progresses at a pressure of about ($10^{-3}$–$10^{-4}$ mbar) $1 \times 10^{-1}$–$1 \times 10^{-2}$ Pa. An arc discharge is ignited between the cathode of main discharge 5 and anode of main discharge 3 (which are preferably separated by a voltage of about 200 V) by means of auxiliary discharge between the cathode of auxiliary discharge 7 and the cathode of main discharge 5 and the anode of auxiliary discharge 4 surrounding the cathode of main discharge 5.

The auxiliary discharge is ignited by means of ignition electrode 6, made in the form of an annular ring as described earlier and disposed between anode 4 and cathode 5 of the auxiliary discharge. Formation of Tetracarbon film upon a substrate surface such as, for example, the surface of a medical implant which will be exposed to living tissue following implantation within an organism progresses by the condensation of short carbon chains from a carbon plasma sheaf upon the substrate surface. The sheaf of carbon plasma is formed in a pulsed arc discharge. The evaporation of the carbon plasma sheaf from the graphite cathode of main discharge 5 is caused by local heating of the graphite surface by electron bombardment to T=3000° C. Chains of carbon atoms, $C_n$ (where n=1, 2, 3, 5, 7, . . . ), thus formed in the plasma sheaf are directed by electrodes to impinge upon the surface of the substrate where the polycondensation of carbon chains takes place. The condensation includes chain lengthening due to interchain end to end bonding. The electronic temperature of the carbon chain plasma should not exceed the energy required to break the covalent sp double bonds in the carbon chains in order to avoid the formation of non-chain carbon having the short-range order of diamond or graphite.

Capacitor 11 is charged to 200 volts by a power supply 10 which is connected in parallel to the corresponding plates of capacitor 11. Capacitor 11 and inductance 12 are series-connected in the electric circuit of the main discharge and limit the rate of increase of the discharge current pulse. The anode of main discharge 3 is constructed as a "squirrel cage", i.e. with two identical parallel rings interconnected at points along their periphery by rigid metal rods equally spaced along the ring circumference. The anode of main discharge 3 and anode of auxiliary discharge 4, cathode of main discharge 5, ignition electrode 6, cathode of auxiliary discharge 7, and dielectric spacer 8 are disposed coaxially with respect to one another.

A substrate (not shown in FIG. 2) having a surface upon which the formation of Tetracarbon condensate occurs, is attached to a rotatably mountedsubstrate holder 2 positioned within the vacuum chamber 1 20–30 cm behind the anode of main discharge 3. The substrate may be a material such as a ceramic, metal, polymer, silicone rubber, alloy, etc., and may be of any shape. The Tetracarbon coating may be deposited uniformly with high adhesion to any substrate surface contour, including concave and sharply convex contours, having a radius of curvature greater than about 10 $\mu$m. The substrate (not shown) is mounted on the substrate holder 2 which, during the course of film deposition, completes a planetary orbital trajectory, rotating about an orbital axis indicated by + in FIG. 2 while simultaneously revolving around the substrate holder axis (not shown) which is inclined with respect to the orbital axis + and shown more clearly in FIGS. 6a and 6b.

During the entire cycle of Tetracarbon deposition, the substrate surface supporting the growing film is irradiated with ions of an inert gas 9a, such as argon and/or nitrogen. Suitable inert gas ions 9a are formed in the ion source 9 housed within a side compartment and communicating with the interior of the vacuum chamber 1 through an aperture 9b. The aperture 9b is suitably dimensioned to provide passage of an ion beam which will impact the substrate surface at all orbital positions of the substrate. Gas ion sources are well known in the art and are generally two-electrode systems consisting of a cylindrical cathode with a circular hole through which the ion beam passes and a coaxial ring-shaped anode. The energy of the ion beam irradiating the substrate has initial energy ranging from 150 eV up to 2000 eV to prevent formation of non-linear carbon structures on the substrate surface. The compensated currentless carbon plasma sheaves, formed outside the area of arc discharge gap, have a density of $5 \times 10^{12}$–$1 \times 10^{14}$ cm$^{-3}$, a duration of 200–600 $\mu$sec, and a pulse repetition rate of 1–5 Hz. These parameters are determined experimentally, but generally will depend upon the particular configuration of the ignition electrodes, the electrical circuit of the plasma generator, (including the storage capacitor), the limiting inductance and the three-stage ignition scheme.

The method for manufacturing of Tetracarbon and the apparatus therefor presented hereinabove allows the deposition of a continuous Tetracarbon film upon the surface of many diverse materials (rubber, polymers, ceramics, metals, and alloys; particularly titanium alloys) and upon complex contoured surfaces having micron-sized hollows therein and protrusions therefrom. Non-turbostratic Tetracarbon films have excellent substrate surface adhesion, continuity, and uniformity particularly for a substrate such as medical grade vulcanized silicone elastomer or a semiconductor surface such as prime silicon wafer.

Elemental, naturally occurring carbon is generally regarded as a biocompatible material. However preliminary experiments indicate that the physical characteristics of the Tetracarbon structure render it even more biocompatible than naturally occurring forms of polymeric carbon. The layered, linear-chain non-turbostratic structure of Tetracarbon film may permit the coating to interact with atmospheric substances, such as water, nitrogen, oxygen to cause reassemblage of the film. The atoms of oxygen, nitrogen, H$^+$ and OH$^-$ ions are bonded to free valences of carbon atoms at the ends of the chains and the formation of such bonds mediates reassemblage. In a living organism, these end-groups which are bonded to a terminal carbon atom of a carbon chain may be replaced by other groups which allows reassemblage in a manner which is controlled by the organism.

Figures 4, 5:
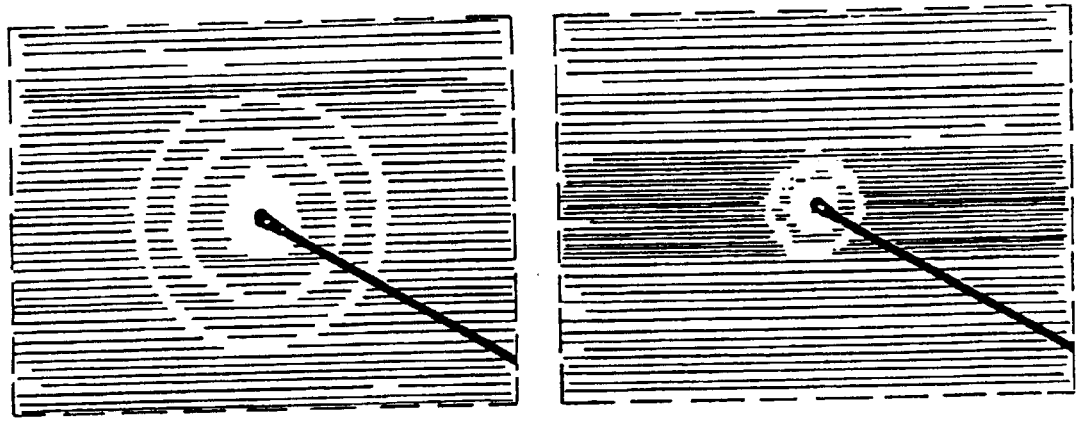
FIG. 4 shows the electron diffraction pattern of a turbostratic carbon film with the direction of the axis of the electron beam perpendicular to the surface of the film.
FIG. 5 shows the electron diffraction pattern of a Tetracarbon film with the direction of the electron beam with respect to the surface of the film identical to that of FIG. 4.

The structural difference between the parallel, non-turbostratic linear chains of covalently double-bonded sp carbon atoms comprising a Tetracarbon layer and the structure of a turbostratic film comprising chains of sp2 carbon atoms arranged to form benzene-like rings is shown in FIGS. 4 and 5. FIG. 4 is an electron diffraction pattern for a turbostratic carbon film. The pattern includes multiple concentric rings, the innermost ring having a diameter which is larger than the diameter of the single ring observed for Tetracarbon which is shown in FIG. 5. In addition to the difference in the electron diffraction patterns observed between turbostratic carbon and Tetracarbon, Auger spectroscopy and Raman spectra provide additional support for the non-turbostratic structure of Tetracarbon.

The regularity of the Tetracarbon polymeric structure within a coating is easily achieved over large areas of substrate surface. The regularity promotes oriented growth of living tissue on the Tetracarbon coating following implantation of a coated substrate beneath the skin. Such well-oriented ingrowth of simple proteins on Tetracarbon may be referred to as "bioepitaxy". Although the reason for bioepitaxy is unknown, it is possible that within a living organism a Tetracarbon coating may rearrange itself, aligning to accommodate atoms or functional groups on a protein adsorbed on the film.

Tetracarbon has a structure and structure-related properties similar to biological tissues. Tetracarbon's unique structure exhibits prospects for further application in microelectronics in connection with the development of its novel properties (functional electronics) based on the simulation of properties and processes in a living organism. Tetracarbon consists of a plurality of identical bent carbon chains with bending randomly oriented relative to the chain axis. As a result, the carbon chains form close-packed layers, each layer being randomly shifted in a direction normal to the carbon chain axes (shown schematically in FIG. 1D). Since the carbon chains within a layer are parallel and close-packed, the bendings of the neighboring chains being correlated and positioned in one plane and in one direction, the translation-symmetrical 2D-hexagonal lattice is formed as shown at FIG. 1D. This regularity of Tetracarbon structure may be localized within a portion of a layer referred to as a "regular zone" having a variable size broadly in the range of about 1000 Angstroms square. Within a regular zone the thickness of each layer of Tetracarbon is uniform, but the thickness of one regular zone may be different from the thickness of other zones. The accumulation of "regular zones" over a substrate surface form the mosaic structure characteristic of Tetracarbon coating.

The formation of structure of a Tetracarbon layered film is a complicated process involving a delicate balance of multiple large opposing forces arising from intermolecular steric strain due to ion-induced carbon chain bending, electrical charge distribution and van der Waals forces to minimize the free energy. The resulting Tetracarbon layer coating the surface of the substrate is a mosaic pattern of adjacent interacting regular zones, each regular zone comprising a large number of close packed parallel carbon chains projecting substantially away from the substrate surface and having a regular zone "thickness" which may be different for adjacent regular zones.

Ion beam irradiation of a substrate surface is essential for achieving Tetracarbon non-turbostratic deposition. Ion irradiation of the surface of the substrate must occur prior to the attachment of one end of the carbon chains thereto to form an innermost Tetracarbon layer. The bombardment of the substrate surface with gaseous ions such as argon or nitrogen creates centers of condensation on the substrate surface to which the carbon chains in the plasma flux may be attached. Short carbon chains (from 1 up to 5 carbon atoms each) are formed in the carbon sheaf without any interaction of the chains with the $Ar^+$ ion beam. These short chains are attached to the substrate so that the carbon chains are growing, but their structure is unstable.

According to quantum mechanical calculations, bends within the carbon chains will enhance the structural stability of the film. As a hypothesis, it is possible that the ion beam irradiation of the substrate surface forms bends in the attached carbon chains which may stabilize the growing chain ensemble. The bending of the linear sp carbon chains in a layer of Tetracarbon film is believed to be due to the resonance charge exchange process between $Ar^+$ and carbon atoms in a condensed chain. As a result, an electron is taken away from a carbon atom and the double bond between the stripped carbon atom and another carbon atom becomes a single bond. This configuration is unstable and the requirement for minimization of energy leads to chain bending, deformation and the association of negative charge on the neighboring atom. Such a bend is called a neutral solitone, which may be able to move along the carbon chain without the input of additional energy. Although in each individual sp-carbon chain these defects (bends) can appear in a random place, the minimization of the total energy of the system of parallel sp-carbon chains leads to their "synchronization", and the bends are all concentrated in one plane—as a double electrical layer, which may play an important role in the reduction of the total energy of the assemblage of carbon chains. Such bendings form interlayer boundaries within a regular zone.

The number of the defects in the chains depends on the energy of ions and their flow density. As a result, the number of the Tetracarbon layers and the "unit length" depend on energy and flow density of the ion beam and on the type of ions employed. As stated above, the layer thickness (and corresponding unit length) is uniform and constant within a zone of regularity. The innermost Tetracarbon layer bonded to the substrate surface may be viewed as being "point welded" to the substrate. Only the terminal end of a portion of the parallel carbon chains within the innermost layer of Tetracarbon are covalently bonded to the substrate surface. The remaining chains within the innermost layer are not bound to the substrate but are held in position relative to the bonded chains by interchain forces.

Biogenic ions interacting with a Tetracarbon film implanted within a living tissue can cause further bending of the carbon chains and a variation of the inter-chain distances. The biogenic ions may penetrate the Tetracarbon film and influence the angle of chain bending thereby changing the local structure of a layer. For example, potassium ions introduced into the carbyne structure (FIG. 1c) induces formation of another crystal lattice due to an intercalation of potassium in the carbyne. It is reasonable to expect that Tetracarbon exhibits similar behavior.

The structure of Tetracarbon reported herein, while not directly observed, is based on studies of the Tetracarbon structure by the methods of electron diffraction, Auger spectroscopy, Raman spectroscopy and transmission electron microscopy. Atomic force spectroscopy of Tetracarbon films is in progress. These methods of analyzing surface structure provide sufficient data to establish the general structure of Tetracarbon, but do not permit the measurement of parameters such as the length of the chains in the innermost layer (i.e.: the layer adjacent to the substrate surface) or the angle of the chain bending.

As stated above, the electron diffraction patterns (FIG. 5) of a thin Tetracarbon film (200 Angstrom thickness) gives the most explicit evidence of Tetracarbon structure. One bright ring comprised of 6 sharp maxima is observed with spacing $d_{10.0}$=4.30–4.37 Å. Other diffraction maxima are absent. The electron diffraction pattern of Tetracarbon impregnated with nitrogen (not shown) is similar to the pattern of non-impregnated Tetracarbon.

Auger spectroscopy of Tetracarbon shows that the percentage by weight of carbon in Tetracarbon is greater than 97% while the concentration of nitrogen and oxygen is less than 3%. Auger spectroscopy of Tetracarbon impregnated with nitrogen shows the concentration of nitrogen ranging from 5% up to 10% and oxygen concentration less than 1%.

Raman spectrum of Tetracarbon impregnated with nitrogen has a sharp maximum at 1525 $cm^{-1}$, another sharp maximum at 2060+10 $cm^{-1}$ corresponding to =C=C=N bonds, and a broad maximum at 2280 $cm^{-1}$ corresponding to —C≡N bonds.

EXAMPLE

Figure 6A:
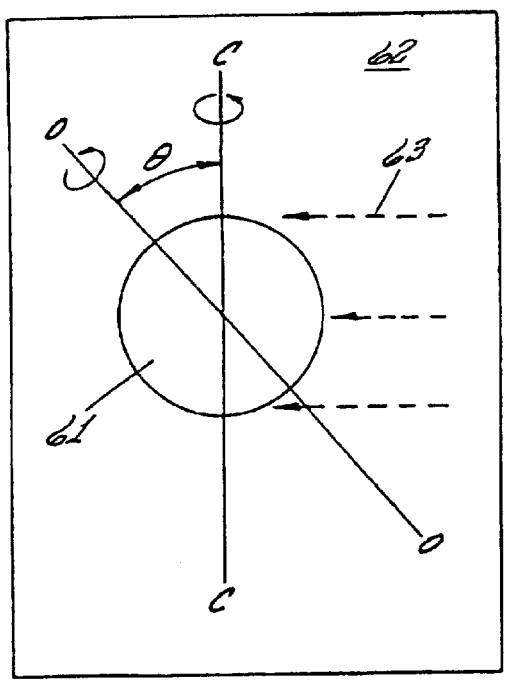
FIG. 6A shows the orientation of the axes of planetary rotation of a spherical substrate relative to the carbon plasma flux.
Figure 6B:
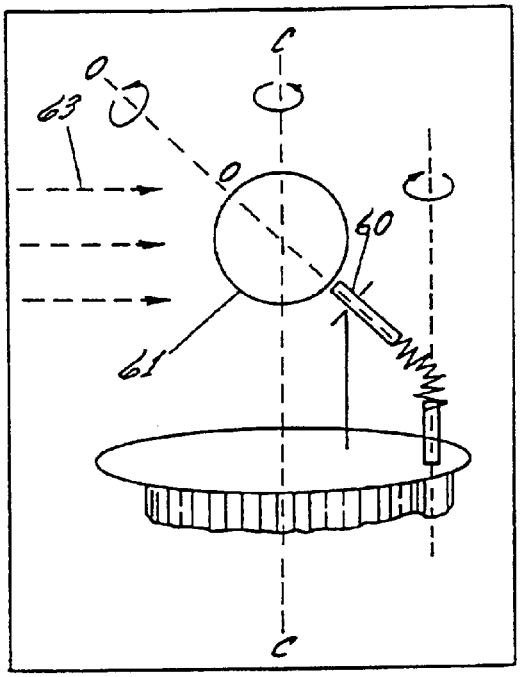
FIG. 6B is a schematic diagram showing the rotation of the substrate during Tetracarbon coating.

Tetracarbon coatings having varying thickness and composition were deposited on an elastomer substrate as described below. With reference to FIGS. 6A and 6B, a spherical silicone shell 61 was inflated, sealed and positioned within a vacuum chamber 62. After the evacuation of air from the chamber, the residual intra-shell pressure maintained the spherical shape of the shell with the diameter of the shell in vacuo 1.5 times greater than the initial diameter of the inflated shell. A substrate holder 60 was designed to support the spherical, silicone shell substrate 61 and ensure planetary rotation about C—C and O—O axes with an angle Θ=35° between the axes (FIGS. 6A, 6B). As the substrate revolves about the O—O axis, the O—O axis rotates around the C—C axis. The carbon chain plasma flux 63 shown at the dotted arrows in FIGS. 6A and 6B, propagates in the picture plane. The direction of the Ar ion beam flux (not shown) is oriented normally to the plane of the picture to intersect the beam 63 at the substrate surface. The impulse repetition frequency used for generating the carbon plasma flux was 3 Hz, the impulse duration being 1 msec.

Three distinct types of Tetracarbon coatings were deposited on the surface of the substrate 61. An "X"-type coating refers to a thick film of Tetracarbon deposited using 400 pulses in an argon atmosphere of $10^{-3}$ Pa. A "Y"-type coating is thinner than the X-type coating and is produced by subjecting the substrate surface to 100 pulses of carbon plasma in an argon atmosphere of $10^{-3}$ Pa. A "Z"-type coating refers to a thin Tetracarbon film deposited using 100 pulses in an $N_2$ atmosphere of $10^{-2}$ Pa.

Prior to the deposition of the X, Y, and Z type coatings on the substrate surface, the surface was irradiated by Ar ions having an ion energy of 500 eV for two minutes, the ion current being 200 mA. During carbon film deposition of both the X and Y type coatings the parameters of Ar ion beam irradiation were kept at the same level as before the deposition. For Z-type coating the substrate surface was irradiated by N⁺ ions during carbon chain deposition. The N ion energy was 500 eV and the ion current was 200 mA.

Figure 7:
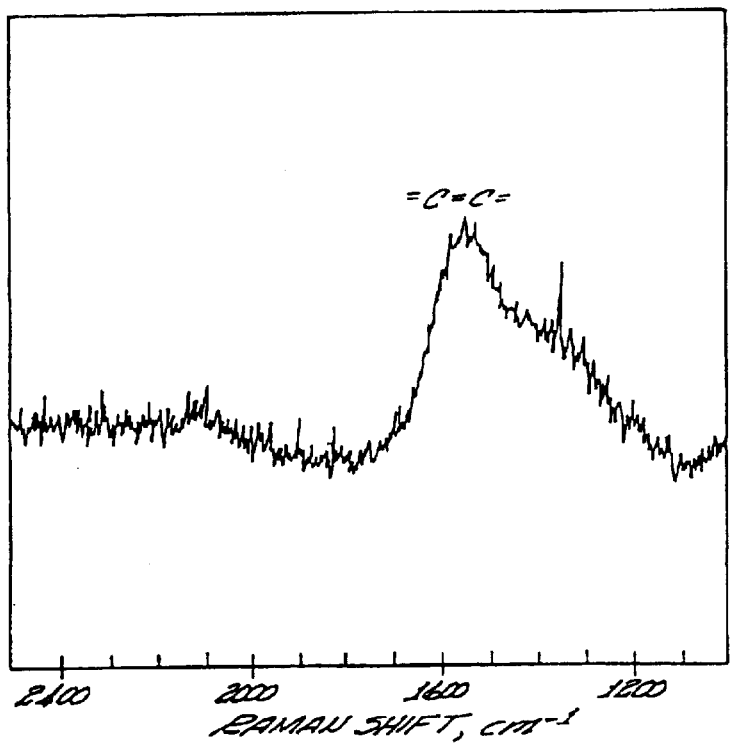
FIG. 7 is the Raman spectra of X and Y-type Tetracarbon coatings.

FIG. 7 shows the Raman spectrum of Tetracarbon for both X and Y coatings (which appeared to be identical). Strong maximum is observed at 1550–1570 cm$^{-1}$. A weak shoulder appears at 1300–1350 cm$^{-1}$ and a very weak maximum is observed at 2070 cm$^{-1}$. These maxima correspond to the linear chain carbon.

FIG. 8 presents the Raman spectrum of Z-type Tetracarbon film impregnated by nitrogen. There are two strong maxima at 1550–1570 cm$^{-1}$ and 1350–1370 cm$^{-1}$ and two weak maxima at 2300 and 2070 cm$^{-1}$. This spectrum corresponds to the linear chain carbon and to C≡N stretching vibrations.

The distribution of film thickness h was measured by optical transmissivity. The carbon film transmittance T is determined as follows:

$$T = I/I_o$$

where $I_o$ is the intensity of incident light;

I is the intensity of light after passing through the film.

The experimental film thickness h is seen to be proportional to –Log (T) as illustrated in FIG. 10 where –Log (T), determined from a transmission measurement of Tetracarbon reference films deposited by 0, 100, 200, 300, 400 pulses is plotted as a function of the number of pulses N.

To find the thickness distribution of Tetracarbon films at the spherical surface of the substrate the transmittance of the Tetracarbon coating is measured as a function of angles A and B (FIG. 11) where angle A was measured from the 0—0 axis (FIG. 9), and angle B is the azimuth angle of a point on the surface. Measurements performed on the X-type film show that the film thickness does not depend on angle B and depends only on angle A as shown in FIG. 11. In FIG. 11, the crosses "x" correspond to the measured thickness while the solid line is the theoretically calculated thickness data for Θ=35°. The theoretical thickness distribution is in accord with the experimental data with the exception of the area near A=180° where the substrate holder was positioned which causes a thinner film deposition therearound. The maximal film thickness is at the equator (A=90°) and the minimal at the bottom of the shell where the gripping device was affixed to the shell. The maximum thickness is approximately 4 times thicker than the minimum thickness.

The following expression was used for theoretical estimations of a film thickness T at the spherical surface rotated around two axes simultaneously in the manner shown in FIG. 6a:

$$T(a) = \int \int [(\sin (f) \cdot \cos (p) + \sin (p) \cdot \cos (\Theta) \cdot \cos (f)) \cdot \sin (A) - \cos (A) \cdot \sin (\Theta) \cdot \cos (f)] df\, dp$$

where the integration is over all angles f and p where the integrated function is positive and Θ=35°. The results of theoretical calculations of Tetracarbon film thickness as a function of the Θ angle are presented at FIG. 12 for different angles Θ=0°, 30°, 45°, 60°, 90°. From this figure one can conclude that if Θ is kept within the range 45°–60°, the film thickness will be the most uniform.

A representative list of medical products which can be enhanced by Tetracarbon coating are presented in Table 2. Some of these applications are under development (mostly pre-clinical trials). It is reasonable to expect that Tetracarbon coating will enhance the substantial parameters of these potential products.

TABLE 2

Potential Medical and Consumer Products with Tetracarbon Coating:

| N | Products with Tetracarbon Coating | What Critical Properties could be Enhanced by Tetracarbon coating | Stage of Development |
|---|---|---|---|
| 1 | Silicone implants-soft tissue prosthesis. | Biocompatibility (thinner capsule, reduces probability of irritation and rejection) | pre-clinical animal trials under way |
| 2 | Metal implants (Ti, stainless steel)-rods for osteosynthesis, dental implants, etc. | Biocompatibility (reduces probabilities of inflammation, tissues irritation, implant rejection) | pre-clinical trials are under way. |
| 3 | Polymer implants, including the internal ear bones prosthesis | Biocompatibility (reduces probabilities of inflammation, tissues irritation, implant rejection), thinner connective tissue formation | pre-clinical trials are underway |
| 4 | Catheters-especially for prolonged introduction, tracheotomy catheters, etc. | Biocompatibility, thromboresistivity, atraumatic introduction thanks to reduced friction coefficient | laboratory mechanical tests |
| 5 | Blood vessel grafts | Thromboresistivity (prevents thrombosis), Biocompatibility | pre-clinical animal trials |
| 6 | Sutures with (or without) needles | Biocompatibility, atraumatic sewing thanks to reduced friction coefficient prevents rough connective tissue formation-especially important for ophthalmological surgery | laboratory mechanical tests |
| 7 | Artificial lens | Biocompatibility (reduces probabilities of inflammation, tissues irritation, lens rejection), enhances UV protection, prevents rough connective tissue formation | pre-clinical animal trials |
| 8 | Contact lens | Biocompatibility (reduces probabilities of inflammation, tissue irritation, UV protection | laboratory mechanical tests planned |
| 9 | Contraceptive spirals | Biocompatibility (reduces probability of inflammation, tissue irritation), prevents scars formation | idea |

TABLE 2-continued

Potential Medical and Consumer Products with Tetracarbon Coating:

| N | Products with Tetracarbon Coating | What Critical Properties could be Enhanced by Tetracarbon coating | Stage of Development |
|---|---|---|---|
| 10 | Metal consumer goods in permanent contact with skin: bracelets of watches rims of glasses, jewelry | Biocompatibility, reduced irritation | idea |

While particular embodiments of the present invention have been illustrated and described, it would be obvious to those skilled in the art that various other changes and modifications can be made without departing from the spirit and scope of the invention. For example, nitrogen may be mixed into argon flow. The two gases are directed into the vacuum chamber with controlled flow rates. An ion bean other than Argon can be used, such as, for example, He or Ne, with the energy of the beam adjusted accordingly. In addition, the geometry of the electrodes and their operating parameters may be varied to adapt the apparatus for providing a coating having desirable properties for a particular application. It is therefore intended to cover in the appended claims all such changes and modifications that are within the scope of this invention.

What we claim is:

1. A medical implant adapted for implantation within a mammal and having a tissue facing surface wherein at least a portion of said tissue facing surface has a non-turbostratic, two-dimensionally ordered, densely packed, linear chain carbon coating affixed thereto comprising a plurality of linear carbon chains, each said carbon chain having an inner end adjacent to said tissue facing surface and an outer end in opposition thereto and a carbon chain axis therebetween wherein said carbon chain axis is defined as being line connecting said inner end and said outer end and wherein said carbon chain axis is oriented substantially perpendicular to a plane tangent to said tissue facing surface at a point on said surface immediately adjacent to said inner end and wherein said inner end of a portion of said plurality of linear carbon chains is chemically bonded to said tissue facing surface of said medical implant.

2. The medical implant of claim 1 wherein said tissue facing surface is a biocompatible elatomer.

3. The medical implant of claim 2 wherein the biocompatible elastomer comprises silicone.

4. The implant of claim 1 wherein substantially each said carbon chain included within said plurality of carbon chains includes at least one carbon atom having an sp electronic state, said at least one carbon atom, C, being represented by the formula A=C=B where A and B are carbon atoms.

5. The implant of claim 2 wherein substantially each said carbon chain included within said plurality of carbon chains includes at least one carbon atom having an sp electronic state, said at least one carbon atom, C, being represented by the formula A=C=B where A and B are carbon atoms.

6. The implant of claim 3 wherein substantially each said carbon chain included within said plurality of carbon chains includes at least one carbon atom having an sp electronic state, said at least one carbon atoms, C, being represented by the formula A=C=B where A and B are carbon atoms.

7. The medical implant of claim 1 which is a soft tissue prosthesis, an osteosynthesis rod, a dental implant, an inner ear bone prosthesis, a catheter, a blood vessel graft, a suture, a suture needle, an artificial lens, a contact lens, or a contraceptive spiral.

* * * * *